(12) United States Patent
Edelmann et al.

(10) Patent No.: US 9,464,995 B2
(45) Date of Patent: Oct. 11, 2016

(54) FIB-SEM ARRAY TOMOGRAPHY

(71) Applicants: Carl Zeiss Microscopy GmbH, Jena (DE); Ruprecht-Karls-Universitaet-Heidelberg, Heidelberg (DE)

(72) Inventors: Martin Edelmann, Aalen (DE); Alexandra F. Elli, Oberkochen (DE); Andreas Schertel, Aalen (DE); Rasmus Schroeder, Heidelberg (DE)

(73) Assignees: Carl Zeiss Microscopy GmbH, Jena (DE); Ruprecht-Karls-Universitaet-Heidelberg, Heidelberg (DE)

( * ) Notice: Subject to any disclaimer, the term of this patent is extended or adjusted under 35 U.S.C. 154(b) by 0 days.

(21) Appl. No.: 14/339,691

(22) Filed: Jul. 24, 2014

(65) Prior Publication Data
US 2015/0036122 A1 Feb. 5, 2015

(30) Foreign Application Priority Data

Aug. 2, 2013 (DE) ........................ 10 2013 215 272

(51) Int. Cl.
*G01N 23/00* (2006.01)
*G01N 21/17* (2006.01)
*G01N 23/225* (2006.01)
(Continued)

(52) U.S. Cl.
CPC .............. *G01N 23/00* (2013.01); *G01N 21/17* (2013.01); *G01N 23/2251* (2013.01); *G01N 23/2255* (2013.01); *G02B 21/34* (2013.01); *G01N 2223/612* (2013.01); *G02B 21/002* (2013.01)

(58) Field of Classification Search
CPC .................................................... G01N 23/00
See application file for complete search history.

(56) References Cited

U.S. PATENT DOCUMENTS

2007/0215802 A1* 9/2007 Ward et al. ................... 250/309
2008/0152207 A1 6/2008 Micheva et al.
(Continued)

FOREIGN PATENT DOCUMENTS

DE 102010052674 A1 5/2012
WO WO 2010/130639 A1 11/2010
(Continued)

OTHER PUBLICATIONS

Extended European Search Report for EP Application No. 14179050.1 dated Nov. 4, 2014.
Lucas et al., "Bridging Microscopes:3D Correlative Light and Scanning Electron Microscopy of Complex Biological Structures", Methods in Cell Biology, vol. III: 325-356 (2012).
(Continued)

*Primary Examiner* — Tarifur Chowdhury
*Assistant Examiner* — Omar Nixon
(74) *Attorney, Agent, or Firm* — Fish & Richardson P.C.

(57) ABSTRACT

Methods and devices for magnified imaging of three-dimensional samples are disclosed. The methods include imaging sample sections of a sample section series using a first particle-optical device. Coordinates of the imaged sample point are acquired and stored in such a way that the coordinates of the imaged sample point can be associated with the respective image of this sample point. The method also includes selecting a volume of interest (VOI), and transmitting the coordinates of the selected VOI to a second particle-optical device. In addition, the method includes imaging the selected VOI by means of the second particle-optical device. A plurality of planes of a sample section are imaged in order to obtain a 3D image of the selected VOI.

28 Claims, 5 Drawing Sheets

(51) Int. Cl.
*G02B 21/34* (2006.01)
*G02B 21/00* (2006.01)

(56) References Cited

U.S. PATENT DOCUMENTS

| | | |
|---|---|---|
| 2010/0059672 A1* | 3/2010 | Zeile .............................. 250/282 |
| 2011/0292385 A1* | 12/2011 | Haustein et al. ............. 356/302 |
| 2012/0126115 A1 | 5/2012 | Heise et al. |
| 2012/0133757 A1 | 5/2012 | Thomas et al. |
| 2013/0081882 A1* | 4/2013 | Lin et al. ...................... 175/428 |
| 2013/0279752 A1 | 10/2013 | Thomas et al. |

FOREIGN PATENT DOCUMENTS

| | | |
|---|---|---|
| WO | WO 2010/136319 | 12/2010 |
| WO | WO 2012/080363 A1 | 6/2012 |

OTHER PUBLICATIONS

Marko et al., "Focused-ion-beam thinning of frozen-hydrated biological specimens for cryo-electron microscopy", Nature Methods, Nature Publishing Group, GB, vol. 4(3):215-217 (2007).

Murphy et al., "Correlative 3D imaging of whole mammalian cells with light and electron microscopy", Journal of Structural Biology, Academic Press US, vol. 176(3): 268-278 (2011).

Maco B et al. (2013): "Correlative in Vivo 2 Photon and Focused Ion Beam Scanning Electron Microscopy of Cortical Neurons", PLOS ONE, vol. 8: Issue 2; Feb. 2013.

Robinson, J.M. et al. (2001): Correlative Fluorescence and Electron Microscopy on Ultrathin Cryosections: Bridging the resolution Gap, The Journal of Histochemistry and Cytochemistry, 49 (7): 803-803, 2001.

\* cited by examiner

FIG.5

FIB-SEM ARRAY TOMOGRAPHY

CROSS-REFERENCE TO RELATED APPLICATION

This application claims priority under 35 U.S.C. §119 to German patent application serial no. 102013215272.8, filed Aug. 2, 2013, the entire contents of which are hereby incorporated by reference.

FIELD

The disclosure relates to methods and devices for magnified imaging of three-dimensional samples.

BACKGROUND

In correlative light and electron microscopy, the light-microscopic imaging is used to seek in a targeted manner sample points which are subsequently intended to be imaged in the electron microscope with a very high magnification and resolution. In the case of two-dimensional images, this correlation can be achieved by the transmission of 2D coordinates from the light microscope to the electron microscope.

However, it is often desired to examine and image the three-dimensional structure of a sample. This is possible with the aid of tomographic methods, in which individual planes of a three-dimensional sample are imaged without superposition. The three-dimensional structure of the sample can then be represented in a 3D reconstruction with the aid of a series of such slice images.

However, the application of tomography in correlative microscopy is connected with difficulties. Although a confocal light microscope can create a 3D image of a three-dimensional sample if the sample is optically transparent, the slices, imaged thus, situated in the interior of the sample are, however, not accessible to imaging via an electron microscope since the sample is generally not transparent to electrons. Therefore, a coordinate transfer of the 3D data obtained in the light microscope to the electron microscope is connected with difficulties and not very expedient.

Moreover, the sample is usually be embedded before observation in the electron microscope in order to make it stable in a vacuum. However, as a result, the sample changes so strongly in terms of the spatial extent thereof that sample points which are defined by three-dimensional coordinates cannot be retrieved without problems. Furthermore, further preparation steps are usually involved for preparing the imaging by electron microscopy, such as e.g. the contrasting of biological samples with heavy metals.

Although it is feasible to fix and embed the sample prior to the examination by light microscopy so that stable coordinates which no longer change between observation by light microscopy and observation by electron microscopy can be defined, this results in heavy metal dyeing already having to be undertaken during the embedding step. This in turn is disadvantageous in that the state of the sample is not ideal for the examination by light microscopy since the light-optical transparency is reduced and the sample material is no longer suitable for fluorescence examinations.

Another solution approach consists in dissecting the sample into sections of the series. The sample is embedded in advance and dissected into electron-transparent ultrathin sections. Here, the sample sections are so thin that the structures thereof have a virtually two-dimensional form. The acquired 2D coordinates are then transmitted from the light microscope to the electron microscope. There is no transmission of 3D data since the three-dimensionality of the data only emerges from combining a plurality of 2D data records to form a 3D reconstruction. Further disadvantages include that highly precise ultramicrotomes with high quality diamond blades are involved and the axial resolution is limited by the section thickness that can be achieved with the employed ultramicrotome. Conventionally, a section thickness of less than 50 nm to 30 nm cannot be achieved by ultramicrotomes.

Methods in which a sample is dissected into sections of the series are known. The sample sections are deposited on a sample carrier in such a way that the sequence thereof is maintained in the section series. For this purpose, the sample sections are arranged in connected chains or so-called "arrays". It is possible to create a 3D reconstruction of the sample on the basis of the images of the ordered sample sections. A disadvantage of this is that the sample is cut into ultrathin slices, i.e. into sections, the thickness of which is at most approximately 200 nm. Moreover, very many or almost all sample sections are imaged and screened when searching for regions of interest. This means that a number of sample sections which contain no structures of interest are also imaged and examined with much expenditure of time.

Processes from correlative microscopy, in which the position of a region of interest (ROI) is defined in one microscope and re-approachable in a further microscope by the transmission of 2D data, are also known. A disadvantage here is that this only succeeds for two-dimensional data, ultrathin sections are used and the resolution in the z-direction is limited by the thickness of the sample sections. By contrast, a resolution in the z-direction of a few nanometers is desirable.

The following documents are known: US 2008/0152207A1; WO 2012/080363 A1; Maco B et al. (2013): "Correlative in Vivo 2 Photon and Focused Ion Beam Scanning Electron Microscopy of Cortical Neurons", PLOS ONE, Vol. 8: Issue 2; and Robinson, J. M. et al. (2001): Correlative Fluorescence and Electron Microscopy on Ultrathin Cryosections: Bridging the resolution Gap, The Journal of Histochemistry and Cytochemistry, 49 (7): 803-803.

SUMMARY

The present disclosure relates to a method for magnified imaging of samples, a device for magnified imaging of samples and a computer program product for a device which images a sample in a magnified manner. In particular, the present disclosure relates to such devices and methods in which sections of the series are imaged in such a way that the user can select volumes of interest of the sample in order to image these volumes in a targeted manner with a high resolution and to establish 3D reconstructions of the sample or of parts of the sample in a targeted manner with a high lateral and axial resolution.

The disclosure provides a method for magnified imaging of a sample, the method including: imaging sample sections of a sample section series via a first particle-optical device, wherein coordinates of the imaged sample point are acquired and stored in such a way that the coordinates of the imaged sample point can be associated with the respective image of this sample point; selecting a volume of interest (VOI); transmitting the coordinates of the selected VOI to a second particle-optical device; and imaging the selected VOI via the second particle-optical device, wherein a plurality of planes of a sample section are imaged in order to obtain a 3D image of the selected VOI. Additional advantageous embodiments of the disclosure are disclosed herein. Moreover, the disclosure relates to a device for magnified imaging of samples via such a method, and to a computer program product which prompts one or more such devices to carry out such a method.

In order to carry out the method according to the disclosure, the sample to be examined is dissected into a series of sample sections. The sample sections can have a section thickness up to several micrometers and are deposited on a suitable sample carrier in such a way that the original localization of the sample sections in the sample is known or can be established at all times.

Then, the sample sections are imaged in a magnified manner in a first particle-optical device, for example a light microscope. To this end, a plane (z-plane) perpendicular to the optical axis of the imaging device is imaged per sample section, wherein the coordinates for each imaged plane are established and stored together with the image. In this manner, at least the x- and y-coordinates (2D coordinates), preferably the x-, y- and z-coordinates (3D coordinates, spatial coordinates), are established for each imaged plane and stored in such a way that the coordinates of an imaged sample point can be associated with the respective image of this sample point. Therefore, this means that coordinates are established and stored for the sample points imaged in the z-planes. To this end, the position of the imaged plane (z-plane) can be determined in relation to markings situated on the sample carrier. These markings serve for referencing the positions of the imaged z-plane in the first and further particle-optical devices.

It is also feasible to image a plurality of optical planes per sample section by virtue of regions of the sample not situated on the sample surface but lying within the sample section volume also being imaged. In other words: the first series of sample sections can also be embodied as series of optical sections. By way of example, this is possible if a confocal light microscope, preferably a confocal laser scanning microscope is used for magnified imaging. Alternatively, a high resolution light microscope or a light-optical reflection microscope or an x-ray microscope or an x-ray tomography scanner can also be used for creating and imaging the optical sections.

What only one z-plane being imaged per sample section means is that a 2D image of the sample section is generated. By contrast, if a plurality of z-planes are imaged per sample section—this is also referred to as a plurality of "optical sections" being generated—this corresponds to a 3D image of the sample section.

A three-dimensional reconstruction of the whole sample or of parts of the sample is created from the 2D or 3D images of the individual sample sections. The 3D reconstruction represents the imaged sample or the imaged part of the sample, wherein the spatial coordinates of the represented sample regions can at all times be associated with the corresponding region of the 3D reconstruction. Likewise, the regions of the 3D reconstruction can at all times be uniquely associated with the corresponding points in the sample.

Now, a volume of interest (VOI) that is to be examined in more detail is selected in the data of the 3D reconstruction. Naturally, it is also possible to select a plurality of VOIs in the 3D reconstruction.

Alternatively, it is also possible to select the VOI on the basis of 2D or 3D images of the sample sections without using a 3D reconstruction in the process. To this end, the VOI is selected by virtue of a region of interest (ROI) being selected e.g. in a 2D image of a sample section. Alternatively, the VOI can also be selected in a 3D image of a sample section.

Then, the position or spatial coordinates, i.e. the 2D or 3D coordinates, of the sample volume represented by the selected VOI are transmitted to a second particle-optical device with the goal of only imaging those sample sections which contain VOIs or parts of VOIs in the subsequent image recording steps.

It is advantageous if the second particle-optical device can image the sample sections with a higher lateral resolution than the first particle-optical device. It is particularly advantageous if the lateral resolution of the second particle-optical device is higher than that of the first particle-optical device by at least a factor of 5, preferably by a factor of 10.

The second particle-optical device can be a particle-optical device operating with charged particles, for example a scanning electron microscope (SEM) or an FIB-SEM combination instrument. The limit of the lateral resolution of a light microscope is usually 200 nm; that of an SEM is 1 nm.

In an electron microscope, for example a scanning electron microscope (SEM), a primary electron beam is generated via an electron source, which primary electron beam is, via a beam guidance system which typically includes an objective lens, directed and focused onto the sample to be examined. The primary electron beam is guided over the sample in a grid-like manner via a deflection apparatus. The primary electrons incident on the sample interact with the material of the sample such that interaction products are released. By way of example, these interaction products can be secondary electrons (SE) or backscattered electrons (BSE). The interaction products are detected by suitable detectors and used for image generation. Depending on the type of detected interaction products, it is possible to generate images with distinct image contrasts.

An FIB-SEM combination instrument should be understood to mean a scanning electron microscope (SEM) which furthermore includes an ion column for generating a focused ion beam. In the ion column, an ion beam which is directed and focused onto the sample is generated via an ion source. Via the ion beam, it is possible to ablate material from the sample or deposit material onto the sample surface in a targeted manner. Secondly, the ion beam can also be used to release detectable interaction products from the sample such that an image of the sample can be generated. These interaction products can be secondary electrons (SE), but also secondary ions or backscattered ions.

In principle, depending on the type of detected interaction products, it is possible to generate images with distinct image contrasts. By way of example, a cathodoluminescence detector can be used for detecting luminescence signals.

Alternatively, an ion combination instrument, for example an FIB-HIM combination instrument, can be used as second particle-optical device. An FIB-HIM combination instrument should be understood to mean a particle-optical device which includes a first ion column for generating a focused ion beam for imaging a sample and a second ion column for generating a focused ion beam for processing the sample. Preferably, helium ions are generated in the first ion column and gallium ions are generated in the second ion column.

It is also feasible to use an ion combination instrument as second particle-optical device, in which ion combination instrument two different types of ions, for example helium and neon ions, are generated in the same ion column, wherein lighter ions such as helium ions are used for imaging and heavier ions such as neon ions or argon ions are used for processing the sample.

In order to prepare the recording of the image in the method according to the disclosure, the sample volume corresponding to the selected VOI is dissected into sample sections via a second section series. Here, these sample sections are generally substantially thinner than the sample sections in the first section series. The sample sections of the second section series can be produced via e.g. an ultramicrotome. Alternatively, the sample material can be ablated step-by-step in thin slices via a focused ion beam, such that a new surface is exposed in each case slice-by-slice.

Each sample section or each section surface, newly exposed in a slice-by-slice manner, is imaged with magnification via the second particle-optical device. Here, the imaging can occur with the aid of the electron beam and/or ion beam.

In a particular embodiment of the method, relatively large volumes which were not selected as VOI can be removed as these do not contain structures of interest. Here, these sample sections or section surfaces exposed slice-by-slice are not imaged. Rather, image recording is only started when a VOI has been exposed or almost exposed. An advantage of the method according to the disclosure is that the volumes defined as VOIs can be approached and imaged in a targeted manner by the particle-optical device. There is no need for imaging sample regions which do not contain any VOI or for screening of sections when seeking VOIs.

A second 3D reconstruction can be created on the basis of the images which were recorded by the second section series. This second 3D reconstruction has a higher lateral resolution since the recordings are established with a higher resolution in the x- and y-directions. Moreover, the second 3D reconstruction has a higher axial resolution since the section thickness of the second section series is substantially smaller than that of the first section series.

In a further step, the second 3D reconstruction can be superposed on the first 3D reconstruction. This creates a correlative 3D reconstruction which combines the various lateral and axial resolutions of the images of the first and the second section series.

Moreover, the distinct image contrasts which were depicted with the aid of the first and the second particle-optical devices can be superposed.

Therefore, the present disclosure is based upon a multi-stage, hierarchic tomography concept, in which, initially, slice images of thin sections are recorded with average resolution, volumes of interest (VOI) are subsequently defined in the sample and, finally, the volume of interest is imaged and optionally reconstructed in a targeted manner with a high lateral and axial resolution. Thus, this means that, over the course of the method, images with ever-high resolution are obtained, while, having the that, the size of the imaged sample areas and sample volumes is reduced. As a result, the work process is accelerated and the amounts of data to be processed do not become too large such that the obtained data can easily be handled by the software during visualization and data mining.

BRIEF DESCRIPTION OF THE DRAWINGS

Exemplary embodiments of the disclosure are explained below on the basis of figures.

DETAILED DESCRIPTION

Figure 1:
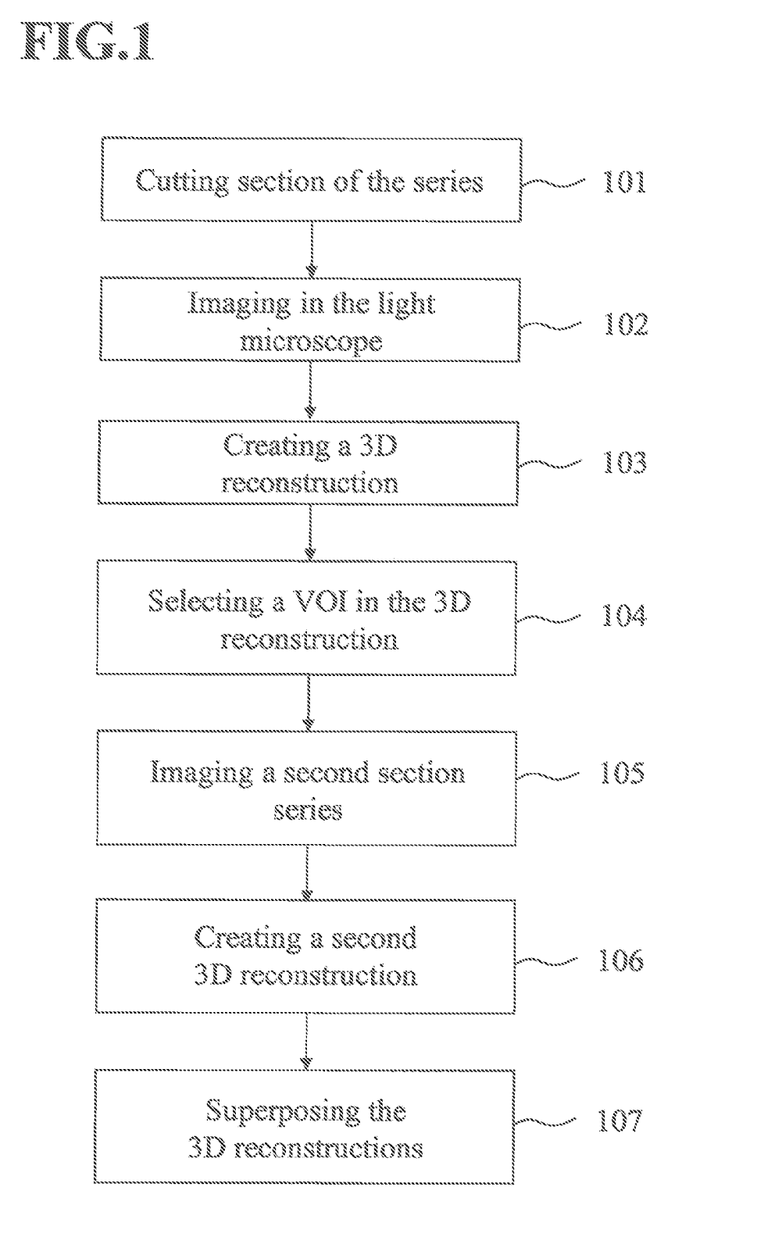
FIG. 1 shows a flowchart of a method according to the disclosure.

FIG. 1 shows a flowchart of the method according to the disclosure. In a first step 101, the sample to be examined is dissected into a series of sample sections. A suitable cutting device, for example a sledge or rotary microtome, can be used to carry out the cutting. In this case, it is particularly advantageous for the cuts to be produced in an automated or semi-automated manner. However, it is also feasible to produce the sections of the series by vibrating microtome, hand-held microtome or as free-hand sections.

Here, it is advantageous that the sample sections can have a section thickness of greater than 1 μm and up to several micrometers, for example 20 μm. Depending on the microscope type subsequently used for recording magnified images, it is also feasible for the sample sections to be thicker than 20 μm, for example 50 μm. If an x-ray microscope is used, the sample sections can even be up to several millimeters thick. Therefore, the sample sections suitable for the method can be produced in a substantially simpler and more reliable manner than semi-thin sections (200-500 nm section thickness) or ultrathin sections (30-200 nm section thickness).

Moreover, it is advantageous that the section thickness may vary. However, the sections are transmissive to light for a 3D recording with a light microscope. If pure 2D recordings are desired, the section thickness can also be greater since the sections need not be transparent to light. However, the sample sections should not be so thick that the structures of interest remain completely hidden within a sample section. Having the that, ultramicrotome sections with a very low section thickness, for example 50 nm or 30 nm, can also be used for the method according to the disclosure.

The sample sections are deposited on a suitable sample carrier in such a way that it is possible to trace back where they were originally localized. By way of example, this can occur by the arrangement in an array. By way of example, such array arrangements are known from US 2008/0152207. The sample carrier can be equipped with appropriate markings which serve for referencing the positions of the sample holder and therefore for determining the position of the sample sections during the examination in the employed particle-optical devices.

By way of example, the sample to be examined can be a tissue sample, but any other type of sample is also feasible. The sample can, in advance, be examined by different processes, for example by wide-field microscopy, laser scanning microscopy, x-ray microscopy or high resolution light-microscopy microscopy (e.g. 3D-SIM). The sample can be fixed in advance by chemical or cryo-processes. It was found to be advantageous for the sample to be embedded by suitable processes before carrying out the method according to the disclosure, for example using an embedding mechanism such as epoxy resin (Epon), paraffin or methyl acrylate, such that the sample is stable in a vacuum and therefore suitable for the subsequent examination in the vacuum chamber of an FIB-SEM combination instrument.

In step 102 of the method, the sample sections are imaged in a magnified manner using a light microscope. Here, use can be made of a conventional light microscope, but also of a light microscope by which a phase contrast or fluorescence contrast can be depicted. Preferably, a confocal light microscope, particularly preferably a confocal laser scanning microscope (LSM), is used for imaging.

At least one z-plane is imaged for each sample section of interest. Since the sample sections have a certain thickness, each sample section can be considered to be a three-dimensional block which, in the z-direction (height of the block), is made up of a plurality of planes, the z-planes, lying parallel to one another. Thus, each sample section can be understood to be a stack of z-planes lying over one another.

In a special embodiment of the disclosure, one of these z-planes, for example the surface of the sample section, per sample section of interest is imaged in a magnified manner. Here, the coordinates of the imaged z-plane are established and stored with reference to the generated image, to be precise in such a way that the coordinates of the imaged sample point can be associated with the respective image of this sample point. Then, the surface of the following sample section and then the surfaces of further sample sections following in the series are imaged and stored in the same manner such that a series of 2D images of the sample sections is obtained.

In another embodiment of the disclosure, a plurality of z-planes are imaged per sample section. This preferably occurs with the aid of a confocal laser scanning microscope. Due to the known confocal principle, it is also possible to image z-planes lying within the sample block. Here, the spatial coordinates of the respectively imaged z-plane are established and stored with respect to the corresponding image. Therefore, a series of images is obtained for the sample section, which images, in the totality thereof, constitute a 3D image of the sample section. Such an image series can be produced not only for one sample section but for a plurality of sample sections such that, overall, a series of 3D images is obtained which, together, represent parts of the sample or the whole sample. Alternatively, use can also be made of a light microscope with an apotome add-on, by which 3D recordings can likewise be generated. The use of 3D x-ray microscopes is likewise possible for creating 3D recordings.

In step 103, a three-dimensional reconstruction of the sample is created from the individual 2D or 3D recordings, i.e. on the basis of the images of the sample sections. The 3D reconstruction represents the sample or part of the sample, wherein the spatial coordinates of the represented sample regions can be associated with the corresponding region of the 3D reconstruction at all times.

If the 3D reconstruction was created from 2D recordings, it is possible to achieve a resolution in the z-direction, i.e. an axial resolution, which corresponds to the section thickness of the sample sections, e.g. 20 µm. In 3D reconstructions from 3D recordings, the achievable axial resolution is determined by the distance of one imaged z-plane from the next imaged z-plane. The distance between the imaged z-planes is usually smaller than the thickness of the sections, and so the resolution of a 3D reconstruction created from 3D recordings is generally better than 20 µm. When using a confocal laser scanning microscope, the axial resolution of the recorded images can be reduced down to 500 nm.

It is also possible initially to carry out prescreening of the sample via 2D recordings in step 102 in order, subsequently, to image the regions of interest in a targeted manner as 3D recordings. An advantage of this is that the z-resolution of the 3D representation of the regions of interest created in step 103 is increased without having to image the whole sample with this high z-resolution, expending much time in the process.

In step 104, a volume of interest (VOI) is selected in the 3D reconstruction. Naturally, it is also possible to select a plurality of VOIs in the 3D reconstruction. Here, a VOI can lie within one sample section or extend over a plurality of sample sections. By geometric calculation processes, the selected VOIs can be associated with two-dimensional regions in the respective sample sections within the section series. Moreover, it is possible to carry out further preparation steps with the sample sections containing a VOI, for example a heavy metal dyeing.

In step 105, the spatial coordinates of the sample volume, which is represented by the selected VOI, are transmitted to a second particle-optical device, for example to an FIB-SEM combination instrument. The goal of transmitting the spatial coordinates of the selected volume is to image only those sample sections in the FIB-SEM combination instrument with a high resolution which contain VOIs or parts of VOIs. This means that it is possible to retrieve the regions (volumes) of interest in a quick and reliable manner, even in three-dimensional samples. Volumes not of interest can be ignored during the examination, bringing with it great savings of time.

The 2D coordinates are transmitted as described in more detail in WO 2012/080363. With reference to a previously defined global coordinate system, at least the x- and y-coordinates of the imaged sample point, advantageously also the z-coordinate (depth), are established, stored and transmitted to the second particle-optical device. It is advantageous to use special sample carriers, for example as described in DE 102010052674A1 and WO 2010/130639A1, for recording the sample sections.

Initially, for the FIB-SEM combination instrument, 2D coordinates for the targeted approach of the VOI on the relevant sections are calculated from the VOI coordinates. This means that the calculated x- and y-coordinates are used as coordinates of approach for the sought-after region in an automated process. Transmitting the z-coordinate moreover renders it possible to determine the z-position (depth) of a VOI. Hence, the position of the VOI within a sample section is transmitted. Moreover, it is possible to transmit the dimensions of each VOI, i.e. the length, width and height of the selected volume.

A second series of sample sections is created for imaging the VOI in a magnified manner. This is brought about in such a way that the sample volume which is represented by the selected volume in the 3D reconstruction is divided into thin slices. To this end, use can be made of an ultramicrotome. The ultramicrotome is preferably miniaturized and situated in the vacuum chamber of the particle-optical device. In a particularly advantageous embodiment, the ultramicrotome is integrated in the vacuum chamber of a scanning electron microscope (SEM). As is conventional in known serial block face imaging, the surface of the sample section (block face), which can be considered as a sample block, is initially imaged in a magnified manner. Then, the uppermost sample slice is removed in an ultrathin manner via the ultramicrotome. The new surface of the sample block, now exposed, is imaged in a magnified manner and once again removed via an ultramicrotome. Then, then newly exposed plane is once again imaged, etc., until a series of images is obtained. The imaging can take place with the aid of the electron beam and/or of the ion beam. The removal of sample sections via an ultramicrotome is advantageous, in particular, if the first section series is embodied as a series of optical sections, for example by virtue of the images being created via an x-ray tomography scanner.

Thus, a series of images is obtained, in which various z-planes of the sample block—which corresponds to a sample section of the first section series—are depicted. The distance between the z-planes in this second section series depends on the capability of the ultramicrotome and is usually approximately 50 nm. In a special embodiment of the method, the distance between the z-planes is approximately 15 nm since the separated sample material need not be kept in the form of a continuous section such that it is also possible to achieve an axial resolution of the recorded z-image stack of 15 nm.

It is also feasible to ablate sample material slice-by slice by processing with a focused ion beam of an FIB-SEM combination instrument. In the process, it is possible to ablate slices of less than 10 nm, for example 5 nm or 3 nm. If the calculations show that a VOI is exposed or cut during the ablation, an image is recorded after each ablation process, for example by scanning with the electron beam. This is how an axial resolution of less than 10 nm emerges for imaging in the FIB-SEM combination instrument. In the slice-by-slice ablation of sample material in the FIB-SEM combination instrument, the respective z-position of the imaged surface is recorded in order later to be able to carry out a 3D correlation.

What is advantageous during ablation with the ion beam is that it is not necessary to ablate the whole area of the sample section. Rather, the user can select a portion as region of interest (ROI). The defined portion then forms the base area of the volume to be ablated since the sample material situated in this portion and in the volume lying therebelow is ablated in a targeted manner via the ion beam. In a preferred embodiment, ablation with the ion beam takes place by virtue of the ion beam being incident perpendicularly on the sample section. In another preferred embodiment, the ablation with the ion beam takes place by virtue of the ion beam being incident parallel with the longitudinal direction of the sample section on the sample section. In a further advantageous embodiment, the sample sections are provided with an electrically conductive coating via electron beam or ion beam deposition.

In step 106, a second 3D reconstruction is created on the basis of the images which were recorded of the second section series. As a result of the axial resolution achievable in the FIB-SEM combination instrument, voxels with an edge length of 5 nm or less can be depicted in the second 3D reconstruction.

Moreover, with step 107, there optionally is the possibility of superposing the first and the second 3D reconstruction, i.e. superposing the 3D data record recorded with the light microscope and the 3D data record recorded with the electron microscope. The algorithm for this is substantially simplified by virtue of the first assignment already being predetermined in the z-direction by the section thickness of the semi-thin sections.

As a result of the superposition, a correlative 3D reconstruction is created, which combines the various lateral and axial resolutions of the images from the first and second section series. Moreover, as a result, it is possible to combine distinct image contrasts which supply different image information. By way of example, certain sample points can be specifically marked and imaged in the light microscope via fluorescence contrast, without, however, the structure of the sample being imaged. By contrast, the electron microscopic image or the electron microscopic 3D reconstruction supplies information about the ultra-structure of the sample, but no fluorescence information. Only the superposition of the 3D reconstructions renders it possible to localize the marked points within the ultra-structure of the sample.

Figure 2:
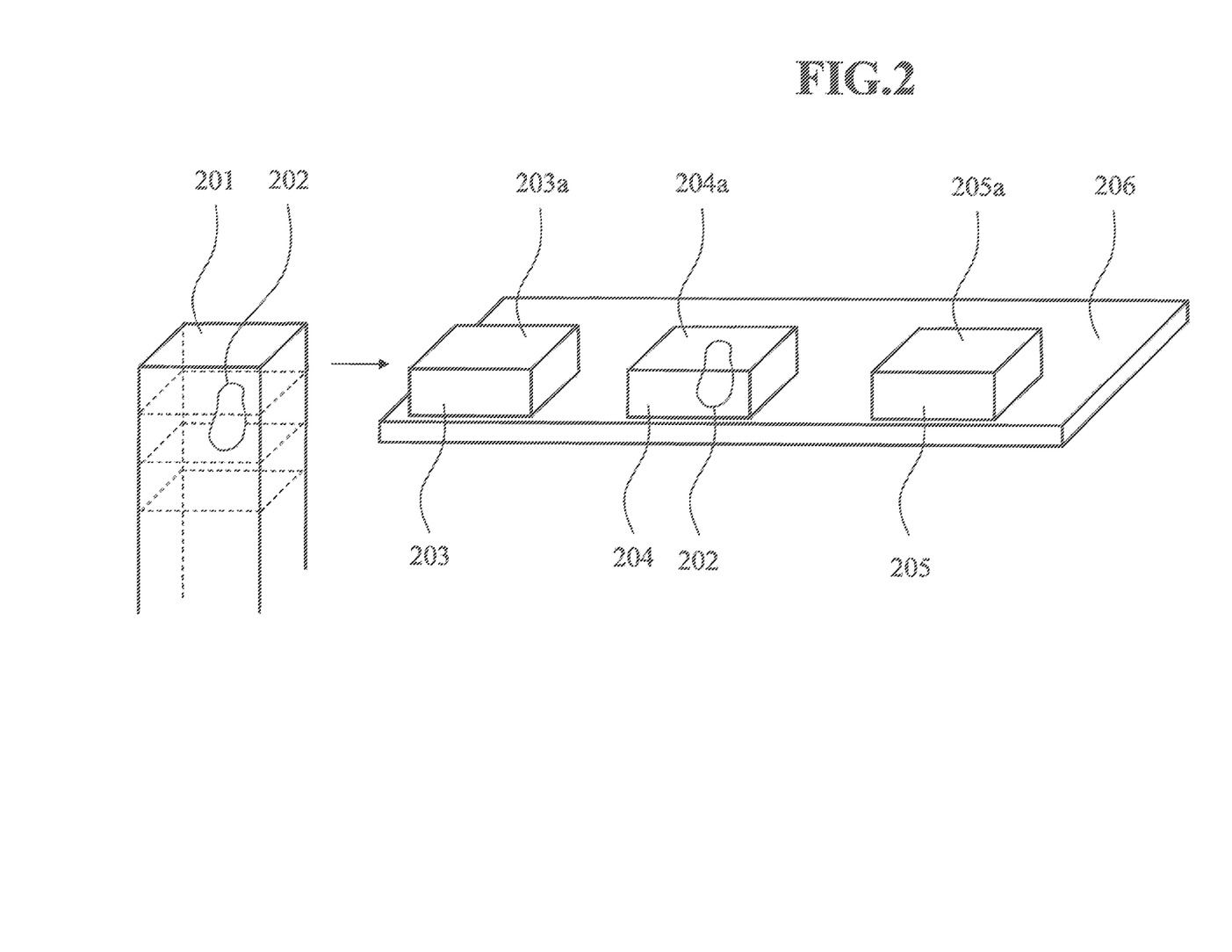
FIG. 2 schematically shows an advantageous embodiment of part of the method according to the disclosure.

FIG. 2 schematically shows an advantageous embodiment of the steps 101 and 102 according to the method. In the interior thereof, the sample 201 to be examined contains a structure of interest 202. The sample 201 is cut into a series of sample sections 203, 204, 205 (three sample sections are shown here in an exemplary manner). The sample sections 203, 204, 205 are deposited in an ordered manner on the sample carrier 206 and imaged in a magnified manner in a first particle-optical device, for example a conventional light microscope (not depicted here). Here, a z-plane 203a, 204a, 205a is imaged in a magnified manner for each sample section 203, 204, 205. Advantageously, the imaged z-plane 203a, 204a, 205a respectively is the exposed surface of the sample section. In the subsequent method steps 103, a 3D reconstruction of the sample 201 is calculated on the basis of the recorded images, which can be displayed on a monitor and stored in an evaluation and control unit.

Figure 3:
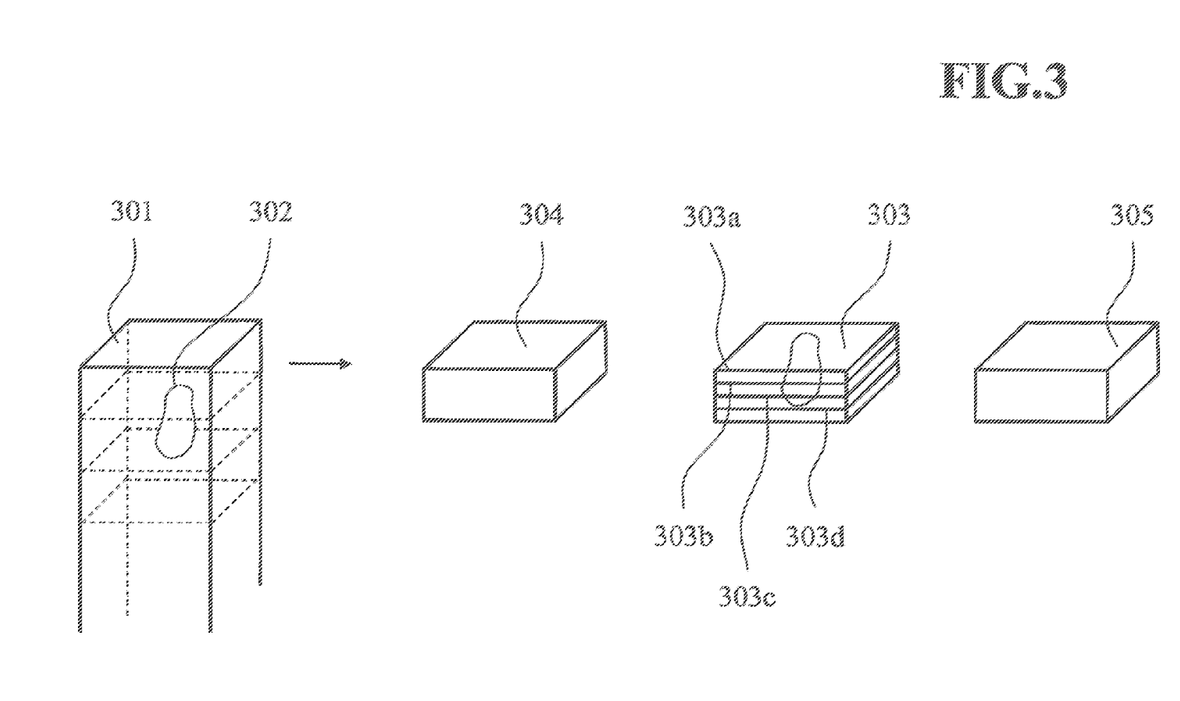
FIG. 3 schematically shows another advantageous embodiment of part of the method according to the disclosure.

FIG. 3 schematically shows another advantageous embodiment of the steps 101 and 102 according to the method. Here too, the sample 301 to be examined contains a structure of interest 302 in the interior thereof. The sample 301 is cut into a series of sample sections 303, 304, 305 (three sample sections are shown here in an exemplary manner). The sample sections 303, 304, 305 are imaged in a magnified manner in a first particle-optical device, for example a confocal laser scanning microscope (not depicted here). Here, a plurality of z-planes are imaged in a magnified manner for each sample section 303, 304, 305. This is shown in an exemplary manner using the first sample section 303 with four depicted z-planes 303a, 303b, 303c, 303d. Naturally, it is also possible for a different number of z-planes to be imaged. In the case of a typical section thickness of 20 μm and an axial resolution of 500 nm, which can usually be achieved using a confocal laser scanning microscope, this for example results in 40 z-planes per sample section. In this exemplary embodiment, the recorded images can also be displayed on a monitor and stored in an evaluation and control unit. In the following method step 103, a 3D reconstruction of this sample section 303 then is created on the basis of the image stack of the various z-planes 303a, 303b, 303c, 303d recorded for a sample section 303. Alternatively, a 3D reconstruction of the examined part of the sample or of the whole sample 301 is created on the basis of the image stacks recorded for a plurality of sample sections 303, 304, 305.

Figure 4:
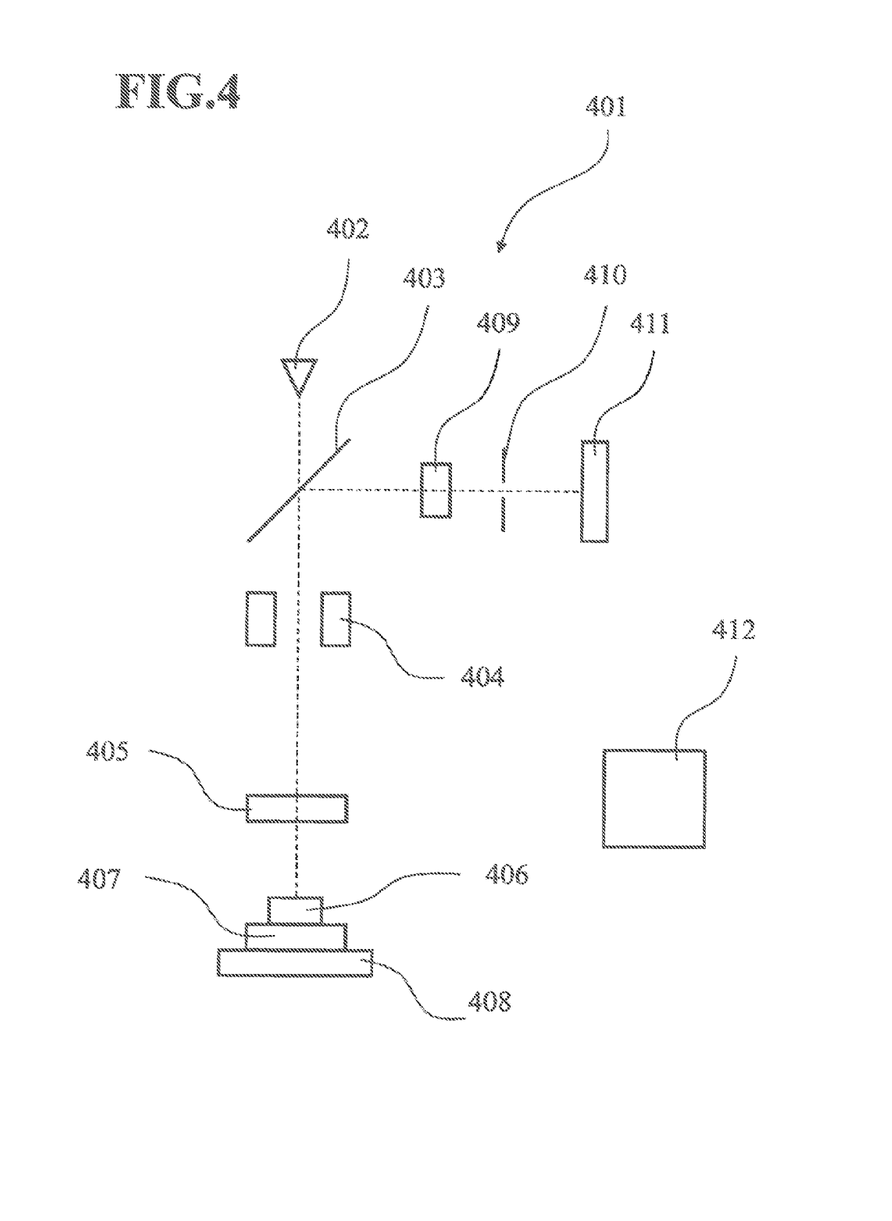
FIG. 4 schematically shows the design of a particle-optical device suitable for carrying out the method according to the disclosure.
Figure 5:
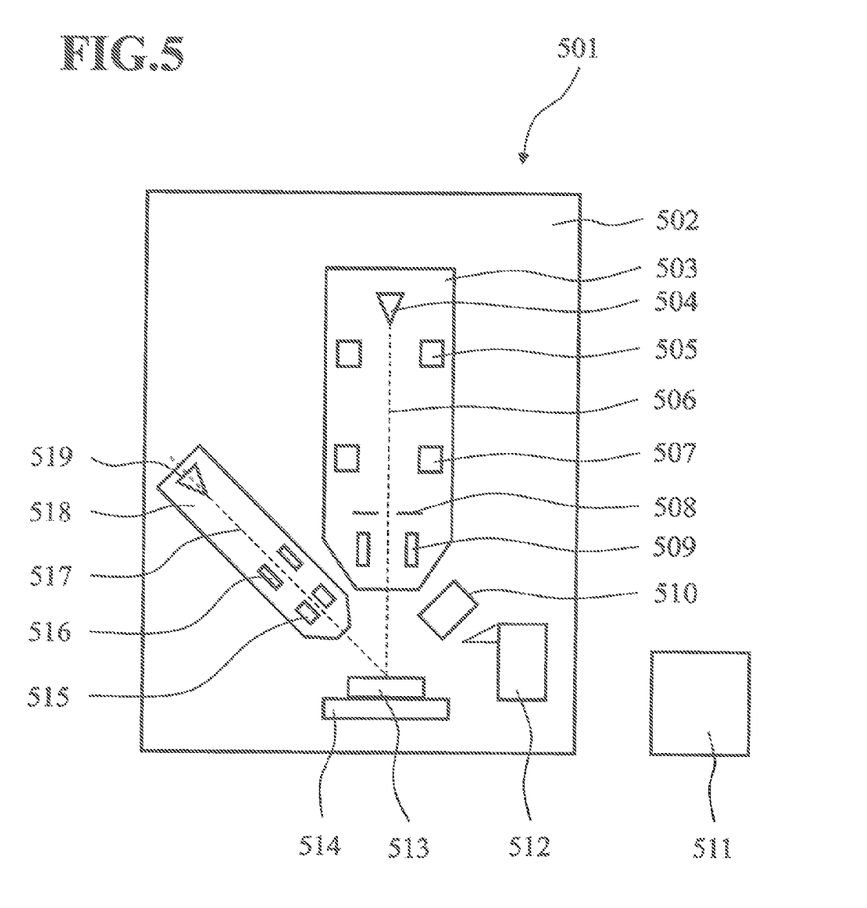
FIG. 5 schematically shows the design of a further particle-optical device suitable for carrying out the method according to the disclosure.

FIGS. 4 and 5 show embodiments of the device according to the disclosure. The device is embodied to carry out the method depicted in FIG. 1. The device includes a first particle-optical device and a second particle-optical device, wherein the constituents of the device are configured to carry out the method according to the disclosure.

As depicted in FIG. 4, the device in a particularly advantageous embodiment includes a laser scanning microscope 401 with a sample carrier 407 which can be e.g. a slide. The sample carrier 407 is embodied in such a way that it—together with the sample sections 406 arranged thereon—can be transferred into a second particle-optical device, for example an FIB-SEM combination instrument. The sample carrier 407 is attached to a movable sample receptacle 408 in such a way that the sample carrier 407 can be displaced in at least the x- and y-direction by the movement of the sample receptacle 408, which is controlled by the evaluation and control unit 412.

It was found to be advantageous if the possible positions of the sample receptacle 408 are incremented and the sample receptacle 408 is calibrated in such a way that the position and angle coordinates can be read out. It is particularly advantageous if the sample receptacle 408 is provided with markings for determining the position.

The laser scanning microscope 401 includes a light source 402, which generates a beam of light which is guided in the direction of the sample section 406 via a beam splitter 403. The laser scanning microscope 401 furthermore includes an objective system 405 for focusing the light beam.

The interaction products emitted by the sample 406 are guided via a beam splitter 403 and a lens system 409 to a detector 411. A pinhole aperture 410, which ensures that only light from a selectable z-plane of the sample volume is detected by the detector 411, is situated between the lens system 409 and the detector 411. The evaluation and control unit 412 controls the deflection system 404 in such a way that the laser beam is scanned over the sample 406. The interaction products emitted by the sample 406 are detected by the detector 411 and depicted by the evaluation and control unit 412 as image data.

The current position of the sample receptacle 408 is transmitted to the evaluation and control unit 412 via the sample receptacle 408. The evaluation and control unit 412 combines these position data with the image data recorded at the same time via the laser scanning microscope. Thus, this means that the magnified images of the sample sections are recorded together with the three-dimensional coordinates of the imaged sample point. To this end, use can be made of specific, local and global coordinate systems, as described in WO 2012/080363.

FIG. 5 schematically shows an FIB-SEM combination instrument 501 with an integrated ultramicrotome 512. The FIB-SEM combination instrument 501 includes a movable sample receptacle 514, onto which the sample carrier described in FIG. 4 can be transferred. The sample section or sections 513 to be examined is/are situated on the sample carrier in a sample chamber 502, in which vacuum conditions are prevalent. The sample receptacle 514 is connected to an evaluation and control unit 511, by which the sample receptacle 514 can be displaced at least in the mutually perpendicular spatial directions x, y and z. The 3D coordinates of the imaged sample points (see FIG. 4) generated in the laser scanning microscope can be transmitted with conventional data transfer processes to this evaluation and control unit 511. Once the coordinates have been transmitted, the sample points imaged in the laser scanning microscope can be approached in a targeted manner by an appropriate movement of the sample receptacle 514 such that these points of the sample 513 can quickly be retrieved in the FIB-SEM combination instrument 501.

The sample receptacle 514 is advantageously embodied as five-axis sample stage. This means that the sample receptacle can be displaced in the x-, y- and z-directions—i.e. in three mutually perpendicular spatial directions—and can be rotated about a tilt axis and a rotation axis, wherein the possible positions of the sample receptacle are incremented. Furthermore, the sample receptacle is calibrated such that the position and angle coordinates can be read out.

Primary electrons are generated in the electron source 504 of the electron column 503, accelerated along the optical axis 506 of the electron column 503, focused by lens systems 505, 507 and curtailed by at least one aperture stop 508. Moreover, the electron column 503 includes a deflection system 509, by which the primary electron beam can be guided over the sample 513 in a grid-like manner. The FIB-SEM combination instrument 501 furthermore includes at least one detector 510 for detecting interaction products.

The FIB-SEM combination instrument 501 moreover includes an ion column 518 with an ion source 519, a deflection system 516 and focusing lenses 515. The ions generated in the ion source 519 are accelerated along the optical axis 517 of the ion column 518 and focused such that the ions are incident on the sample section 513 in a focused manner and can be used to ablate material of the sample section 513.

The disclosure furthermore relates to a computer program product which includes a sequence of control commands which, when executed by an evaluation and control unit 412, 511, prompt the device 401, 501 to carry out the method according to the disclosure.

It is also feasible for a first computer program product to prompt a first device, for example a laser scanning microscope, to execute certain steps of the method according to the disclosure and for a second computer program product to prompt a second device, for example a FIB-SEM combination instrument, to execute further steps of the method. Here, the first and the second computer program products are configured in such a way that the two computer program products are able to interact such that all steps of the method according to the disclosure can be executed.

In an advantageous embodiment, the first particle-optical device and the second particle-optical device differ from one another. It is also feasible for the first and the second particle-optical devices to be connected to one another.

LIST OF REFERENCE SIGNS

101 Step: Cutting a first series of sample sections
102 Step: Imaging sections of the series in the light microscope
103 Step: Creating a 3D reconstruction
104 Step: Selecting a volume of interest (VOI)
105 Step: Imaging a second series of sample sections
106 Step: Creating a second 3D reconstruction
107 Step: Superposing the 3D reconstructions
201 Sample
202 Structure of interest
203 First sample section
203a z-plane of the first sample section
204 Second sample section
204a z-plane of the second sample section
205 Third sample section
205a z-plane of the third sample section
206 sample carrier
301 Sample
302 Structure of interest
303 First sample section
303a First z-plane of the sample section
303b Second z-plane of the sample section
303c Third z-plane of the sample section
303d Fourth z-plane of the sample section
304 Second sample section
305 Third sample section
401 Laser scanning microscope
402 Light source
403 Beam splitter
404 Deflection system
405 Objective system
406 Sample section
407 Sample carrier
408 Sample receptacle
409 Lens system 410 Pinhole aperture
411 Detector
412 Evaluation and control unit
501 FIB-SEM combination instrument
502 Sample chamber
503 Electron column
504 Electron source
505 First lens system
506 Optical axis of the electron column
507 Second lens system
508 Aperture stop
509 Deflection system
510 Detector
511 Evaluation and control unit
512 Ultramicrotome
513 Sample section
514 Sample receptacle
515 Focusing lens
516 Deflection system
517 Optical axis of the ion column
518 Ion column
519 Ion source

What is claimed is:

1. A method, comprising:
using a first particle-optical device to image sample sections of a series of sample sections to generate a first series of images, coordinates of an imaged point of the sample being acquired and stored so that the coordinates of the imaged point of the sample are associated with the image of the point of the sample;
generating a first 3D reconstruction based on information in the first series of images, the first 3D reconstruction being a reconstruction of at least a portion of the sample;
selecting a volume of interest of the sample (VOI) based on information in the first series of images;
transmitting the coordinates of the selected VOI to a second particle-optical device; and
using the second particle-optical device to image a plurality of planes of a sample section that contains the selected VOI to generate second series of images; and
generating a 3D image of the selected VOI based on information in the second series of images.

2. The method of claim 1, wherein the VOI is selected based a region of interest selected in an image of a sample section.

3. The method of claim 1, further comprising generating a second 3D reconstruction on the basis of information contained in the 3D image of the selected VOI, wherein the second 3D reconstruction is a 3D reconstruction of at least a portion of the selected VOI.

4. The method of claim 3, wherein the first 3D reconstruction and the second 3D reconstruction are superposed to form a third 3D reconstruction.

5. The method of claim 1, wherein the sample sections of the series of sample sections are imaged with a first lateral resolution, the selected VOI is imaged with a second lateral resolution, and the first lateral resolution is different from the second lateral resolution.

6. The method of claim 5, wherein the second lateral resolution is at least five times greater than the first lateral resolution.

7. The method of claim 1, wherein the sample sections of the series of sample sections are imaged with a first image contrast, the selected VOI is imaged with a second image contrast, and the first image contrast is different from the second image contrast.

8. The method of claim 1, wherein the first particle-optical device comprises a laser scanning microscope.

9. The method of claim 1, wherein the first particle-optical device comprises an x-ray microscope.

10. The method of claim 1, wherein the second particle-optical device operates with charged particles.

11. The method of claim 1, wherein the second particle-optical device comprises a FIB-SEM combination instrument.

12. The method of claim 1, wherein the second particle-optical device comprises an ion combination instrument.

13. The method of claim 1, wherein the second particle-optical device comprises a FIB-HIM combination instrument.

14. The method of claim 1, further comprising using an ultramicrotome to remove sample material to expose the planes of the sample section imaged by the second particle-optical device.

15. The method of claim 1, further comprising using an ion beam to ablate sample material to expose the planes of the sample section imaged by the second particle-optical device.

16. The method of claim 1, wherein the second particle-optical device has a lateral resolution which is greater than a lateral resolution of the first particle-optical device.

17. The method of claim 1, wherein using the second particle-optical device to image the selected VOI comprises using the second particle-optical device to image only the selected VOI.

18. A device, comprising:
a first particle-optical device; and
a second particle-optical device,
wherein the device is configured so that, during use of the device:
the first particle-optical device images sample sections of a series of sample sections to generate a first series of images, coordinates of an imaged point of the sample being acquired and stored so that the coordinates of the imaged point of the sample are associated with the image of the point of the sample;
a first 3D reconstruction is generated based on information in the first series of images, the first 3D reconstruction being a reconstruction of at least a portion of the sample;
a volume of interest of the sample (VOI) is selected based on information in the first series of images;
coordinates of the selected volume of interest VOI are transmitted to a second particle-optical device; and
the second particle-optical device images a plurality of planes of a sample section that contains the selected VOI to generate a second series of images; and
a 3D image of the selected VOI is generated based on information in the second series of images.

19. A non-transitory computer-readable storage medium storing a computer program product comprising instructions that are executable by an evaluation and control unit to perform operations comprising:
using a first particle-optical device to image sample sections of a series of sample sections to generate a first series of images, coordinates of an imaged point of the sample being acquired and stored so that the coordinates of the imaged point of the sample are associated with the image of the point of the sample;
generating a first 3D reconstruction based on information in the first series of images, the first 3D reconstruction being a reconstruction of at least a portion of the sample;

selecting a volume of interest of the sample (VOI) based on information in the first series of images;

transmitting the coordinates of the selected VOI to a second particle-optical device; and using the second particle-optical device to image a plurality of planes of a sample section that contains the selected VOI to generate second series of images; and generating a 3D image of the selected VOI based on information in the second series of images.

20. A method, comprising:

using a first particle-optical device to image sections of a sample, each section of the sample comprising sample points;

generating a first 3D reconstruction of the sample based on information in the imaged sections of the sample obtained using the first particle-optical device;

selecting a volume of interest (VOI) of the sample based on information in the imaged sections of the sample obtained using the first particle-optical device;

using a second particle-optical device to image a plurality of planes of a sample section that contains the selected VOI based on coordinates of the VOI obtained based on information in the imaged sections of the sample obtained using the first particle-optical device; and generating a 3D image of the selected VOI based on information in the imaged sections of the sample obtained using the second particle-optical device.

21. The method of claim 1, further comprising, before imaging the plurality of planes of the sample section to obtain the 3D image of the selected VOI, slicing the sample section to provide the plurality of planes of the sample section.

22. The method of claim 21, wherein at least one plane of the sample section is less than 10 nm thick.

23. The method of claim 22, wherein the sample section is at least 30 nanometers thick.

24. The method of claim 22, wherein the sample section is at least 200 nanometers thick.

25. The method of claim 22, wherein the sample section is at least 500 nanometers thick.

26. The method of claim 22, wherein the sample section is at least one micron thick.

27. The method of claim 20, further comprising generating a second 3D reconstruction on the basis of information contained in the 3D image of the selected VOI, wherein the second 3D reconstruction is a 3D reconstruction of the selected VOI.

28. The method of claim 27, wherein the first 3D reconstruction and the second 3D reconstruction are superposed to form a third 3D reconstruction.

* * * * *

UNITED STATES PATENT AND TRADEMARK OFFICE
CERTIFICATE OF CORRECTION

| | |
|---|---|
| PATENT NO. | : 9,464,995 B2 |
| APPLICATION NO. | : 14/339691 |
| DATED | : October 11, 2016 |
| INVENTOR(S) | : Martin Edelmann et al. |

It is certified that error appears in the above-identified patent and that said Letters Patent is hereby corrected as shown below:

In the Specification

Column 5, Line 53, delete "the that,"

Column 6, Line 41, delete "the that,"

Signed and Sealed this
Seventh Day of March, 2017

Michelle K. Lee
*Director of the United States Patent and Trademark Office*